United States Patent [19]

Huneke et al.

[11] 4,272,479
[45] Jun. 9, 1981

[54] TESTING TUBE FOR MEASURING CHROMATE AND CHROMIC ACID AEROSOLS IN AIR

[75] Inventors: Karl-Heinz Huneke; Wilfried Laufenberg, both of Lübeck, Fed. Rep. of Germany

[73] Assignee: Drägerwerk Aktiengesellschaft, Fed. Rep. of Germany

[21] Appl. No.: 125,979

[22] Filed: Feb. 29, 1980

[30] Foreign Application Priority Data

Apr. 3, 1979 [DE] Fed. Rep. of Germany ....... 2913283

[51] Int. Cl.³ .................. F01B 23/00; B63H 1/00; G01N 27/62
[52] U.S. Cl. .................................... 422/57; 422/60; 422/61; 422/86; 422/101; 23/232 R
[58] Field of Search .................. 422/59, 83, 86, 88, 422/61, 101, 60; 23/232 R, 232 C; 73/23.1, 23; 252/408

[56] References Cited

U.S. PATENT DOCUMENTS

| | | | |
|---|---|---|---|
| 2,487,077 | 11/1949 | Shepherd | 422/59 |
| 2,908,555 | 10/1959 | Grosskopf | 23/232 R |
| 3,022,141 | 2/1962 | Grosskopf | 422/60 |

OTHER PUBLICATIONS

Furman, H. N., et al., *Standard Methods of Chemical Analysis*, 6th Edition, D. Van Nostrand Co., Inc., New York, 1966, pp. 350–351.

*Primary Examiner*—William F. Smith
*Assistant Examiner*—Chris Konkol
*Attorney, Agent, or Firm*—McGlew and Tuttle

[57] ABSTRACT

A method of testing air for measuring the chromate and chromic acid aerosols therein, comprises, passing the air through a testing tube after each end of the tube has been broken to cause the particles in the air to become entrained on a filter in the tube and, thereafter, breaking an ampoule of sulfuric acid in the tube so that it flows through the filter and dissolves the entrained particles and brings them into contact with a filling material which is also arranged in the tube and which produces a reaction with the particles of chromate and chromic acid which are deposited on the filter. The reaction produces a violet dye, the intensity of the discoloration being directly proportional to the mass of the deposited chromate or chromic acid. The testing tube comprises a closed testing tube having breakoff ends at each end with holders for positioning an ampoule of sulfuric acid upstream in respect to the direction of testing air flowing through the tube of a filling material which includes a granular reagent layer of an earth quartz and diphenyl carbazide, together with a sorption-active silica gel and a subsequent layer of granular quartz.

7 Claims, 1 Drawing Figure

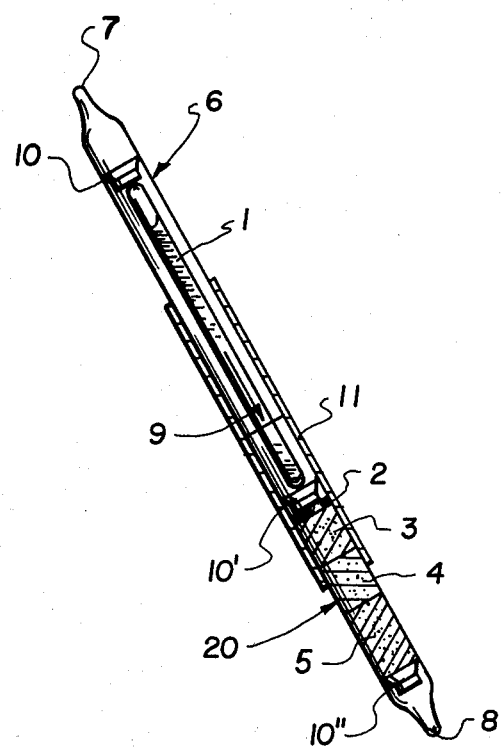

TESTING TUBE FOR MEASURING CHROMATE AND CHROMIC ACID AEROSOLS IN AIR

FIELD AND BACKGROUND OF THE INVENTION

This invention relates in general to a method and apparatus for testing the presence of materials in gases, such as air, and, in particular, to a new and useful testing tube for measuring chromate and chromic acid aerosols in air and to a method of carrying out the testing.

According to the MAK-value list, zinc chromate is a potentially carcinogenic substance. In two other chromates, as well as in chromic acid ($CrO_3$), a carcinogenic is also suspected. Frequent and regular monitoring of these substances is, therefore, absolutely essential.

A known tester for determining chromic acid aerosols uses a special chemically impregnated filter paper which is arranged in a receiver in front of a suction pump. For carrying out the test, the contents of several ampoules is mixed in a plastic injection syringe and is placed on the filter paper as a reagent. The chromic acid aerosol to be determined in the testing air, pumped through the filter paper by means of the suction pump, then leads to discoloration of the charged reagent drop. A color comparison with a standard then determines the concentration value. This known method is complicated because of the necessary preparations, and it requires particularly sufficient preparation time ("M S A Universal Tester", Bulletin No. 0815-6).

SUMMARY OF THE INVENTION

The present invention simplifies the measurement of chromate and chromic acid aerosols in air, which may be carried out even by less qualified personnel, without any special preparations.

In accordance with the invention, a testing tube is provided for measuring chromate and chromic acid in aerosols in the air to be tested. The testing tube comprises a closed glass tube having breakoff points at each end permitting it to be opened for the flow of the air or gas to be tested therethrough. An ampoule or closed tubular container of a breakable glass is mounted within the glass tube and it has diluted sulfuric acid therein which may be released when the ampoule is broken. A filter is arranged in the tube downstream of the ampoule in a position to entrain particles suspended in the air to be tested and a filling is arranged in the glass tube downstream of the filter. When the ampoule is broken, sulfuric acid flushes any entrained particles out of the filter and dissolves them and passes them into the filling material which is located in the glass tube downstream of the filter paper. The filling material comprises a granular reagent layer of an earth quartz enriched with the reagent diphenyl carbazide, followed by a reaction layer of sorptionactive silica gel and a subsequent collecting layer of inert quartz. A covering for the glass tube permits breaking of the ampoule within the glass tube without harm to the operator. The invention provides means to use the testing tube method in an advantageous manner. The testing tube, according to the invention, combines all of the necessary elements in one part. The testing tube method is generally known and permits even less qualified persons to monitor the working place by testing the air. For the measurement, the testing tube points are broken off in a first operation and the air to be tested is conducted with a known suction pump through the testing tube. In a second operation, the ampoule is broken and its contents are pumped with the suction pump into the reaction layer.

In the presence of the chromate and chromic acid aerosol to be determined in the air, the reaction layer shows discoloration. The intensity of the discoloration is directly proportional to the mass of the deposited chromate or chromic acid. Concentrations in a range of 0.05 . . . 1 mg/cu m CrO can thus be reliably determined.

Accordingly, it is an object of the present invention to provide a testing tube for measuring chromate and chromic acid in aerosols in air to be tested which comprises a closed glass tube having breakoff points at each end permitting it to be opened for the flow of gas to be tested therethrough, an ampoule mounted in the tube having one end adjacent one end of the glass tube and an opposite end and having a diluted sulfuric acid therein, a filter in the tube adjacent said opposite end of the ampoule in a position to entrain particles suspended in the air to be tested, and a filling in the glass tube adjacent said filter on the side thereof opposite to said ampoule, said filling comprising a material producing a reaction with the particles to be entrained by the filter and dissolve with the sulfuric acid when the ampoule is broken so that the sulfuric acid entrains and dissolves the particles and directs them into the filling material which produces a reaction to indicate the chromate and chromic acid aerosols.

Another object of the present invention is to provide a method of testing for the presence of chromate and chromic acid aerosols in the air which comprises passing air through a test tube and into a filter to entrain the particles and consequently flushing a sulphuric acid solution through the filter to entrain and dissolve the particles and to bring the entrained particles into contact with a reaction layer, the reaction layer being such as to indicate by a color reaction the presence of chromate or chromic acids in the tested air.

A further object of the invention is to provide a testing tube for measuring chromate and chromic acid aerosols in air which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE of the drawing is a transverse sectional view of a testing tube constructed in accordance with the present invention.

DESCRIPTION OF THE PREFERRED EMBODIMENT

Referring to the drawing in particular, the invention embodied therein, comprises, a testing tube, generally designated 6, which has breakoff points 7 and 8 at each end thereof which may be severed to permit the flow of air to be tested therethrough. The interior of tube 6 contains a filter paper 2 which extends thereacross and entrains particles of the air which are passed through the tube. These particles are dissolved by sulfuric acid which is caused to flow by breaking an ampoule 1 of a breakable material which is located within the glass tube to cause sulfuric acid in the ampoule to flow out of it through the filter to dissolve the particles and then bring them into association with a filling material, generally designated 20, located downstream of the ampoule and the filter paper 2.

Testing tubes for measuring many gases are known. Some of the parts used with the invention are likewise well developed including a sealed glass tube 6 having two breakoff points 7 and 8 at respective ends thereof. A filling, generally designated 20, is held shakeproof in its individual segments between holders or plugs 10, 10' and 10''. The filling 20 proceeding in the direction of flow of the test gas, shown by arrow 9, comprises breakable ampoule 1, which is filled with diluted sulfuric acid disposed between holders 10 and 10' and filter paper 2, a granular reagent layer 3, a granular reaction layer 4, and a granular collecting layer 5, between holders 10' and 10''.

The material of the granular reagent layer 3 is an inert quartz, which is enriched with the reagent diphenyl carbazide. The material of reaction layer 4 is a sorption-active silica gel, and the material of the collecting layer 5 is again an inert quartz. At the level of ampoule 1, the glass tube 6 is covered in a known manner with a shrunk-on cover 11. The cover 11 permits breaking of ampoule 1 after glass tube 6 has been broken.

The measurement is carried out in two steps as follows:

1. After breaking off points 7 and 8, the testing tube is inserted into a known hand suction pump and the air to be tested is then pumped with 40 strokes in the direction of flow 9 through the testing tube. The suspended particles contained in the air, hence, the chromate and chromic acid aerosols, are deposited on filter paper 2.

2. Ampoule 1 is broken and the acid flows in the direction of the filling layers and is subsequently pumped with the suction pump into the reaction layer 4. Here, the chromate or chromic acid deposited on filter paper 2, as well as the diphenyl carbazide in reagent layer 3, are dissolved, and are flushed jointly into reaction layer 4 where the reaction to a violet dye takes place. The intensity of the discoloration of the reaction layer 4 is directly proportional to the mass of the deposited chromatic or chromic acid. By comparison with a color standard, the chromate or chromic acid concentration in the air to be tested is obtained. Collecting layer 5 prevents possible escape of liquid reaction substances to protect the following suction pump.

In accordance with a preferred embodiment of the invention, the quartz of the reagent layer has a grain size of from 0.5 to 0.8 mm and the diphenyl carbazide is present in a concentration of approximately 0.1%. The grain size of the silica gel in the reaction layer is from 0.4 to 0.5 mm. The grain size of the quartz in the collecting layer is 0.5 to 0.8 mm.

While a specific embodiment of the invention has been shown and described in detail to illustrate the application of the principles of the invention, it will be understood that the invention may be embodied otherwise without departing from such principles.

What is claimed is:

1. An improved gas testing device of the type having a glass tube, sealed breakoff points on the opposite ends of the tube, and an ampoule mounted within the tube adjacent one end of the glass tube within the breaking area of one of the breakoff points, an improved arrangement for measuring chromate and chromic acids in air to be drawn through the glass tube comprising, in the direction of flow of the air to be drawn through the tube, the ampoule, a filter paper adjacent the ampoule, a granular reagent layer of quartz impregnated with diphenyl carbazide, a granular layer of silica gel and a granular collecting layer of quartz, and further comprising a quantity of sulfuric acid within said ampoule.

2. A testing tube, as claimed in claim 1, wherein the quartz of the reagent layer has a grain size of from 0.5 to 0.8 mm and the diphenyl carbazide is present in a concentration of approximately 0.1%.

3. A testing tube, as claimed in claim 2, wherein the grain size of the silica gel in the reaction layer is from 0.4 to 0.5 mm.

4. A testing tube, as claimed in claim 3, wherein the grain size of the quartz in the collecting layer is from 0.5 to 0.8 mm.

5. A testing tube, as claimed in claim 1, wherein the grain size of the silica gel in the reaction layer is from 0.4 to 0.5 mm.

6. A testing tube, as claimed in claim 5, wherein the grain size of the quartz in the collecting layer is from 0.5 to 0.8 mm.

7. A testing tube, as claimed in claim 1, wherein the grain size of the quartz in the collecting layer is from 0.5 to 0.8 mm.

* * * * *